(12) United States Patent
Stapelbroek et al.

(10) Patent No.: US 8,448,282 B2
(45) Date of Patent: May 28, 2013

(54) SECTIONED MOUTHPIECE FOR ORAL CARE

(75) Inventors: Martinus Bernardus Stapelbroek, Rolde (NL); Arif Veendijk, Assen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/121,767

(22) PCT Filed: Sep. 22, 2009

(86) PCT No.: PCT/IB2009/054152
§ 371 (c)(1),
(2), (4) Date: Mar. 30, 2011

(87) PCT Pub. No.: WO2010/038171
PCT Pub. Date: Apr. 8, 2010

(65) Prior Publication Data
US 2011/0185525 A1    Aug. 4, 2011

Related U.S. Application Data

(60) Provisional application No. 61/101,712, filed on Oct. 1, 2008.

(51) Int. Cl.
*A46B 9/04* (2006.01)
(52) U.S. Cl.
USPC ............... 15/22.1; 15/167.2; 433/6; 433/41; 433/43
(58) Field of Classification Search
USPC ................... 15/22.1, 167.2, 167.1; 433/6, 41, 433/43, 45, 215; 128/861, 862
See application file for complete search history.

(56) References Cited

U.S. PATENT DOCUMENTS

| | | | |
|---|---|---|---|
| 4,011,616 A | 3/1977 | Kennedy | |
| 4,224,710 A * | 9/1980 | Solow | 15/22.1 |
| 4,505,672 A * | 3/1985 | Kurz | 433/6 |
| 4,977,905 A * | 12/1990 | Kittelsen et al. | 128/861 |
| 5,175,901 A * | 1/1993 | Rabinowitz | 15/167.2 |
| 5,336,086 A * | 8/1994 | Simmen et al. | 433/37 |
| 5,337,435 A | 8/1994 | Krasner et al. | |
| 5,339,832 A * | 8/1994 | Kittelsen et al. | 128/862 |
| 5,511,562 A * | 4/1996 | Hancock | 128/859 |
| 5,829,441 A * | 11/1998 | Kidd et al. | 128/848 |
| 5,895,218 A * | 4/1999 | Quinn et al. | 433/80 |
| 6,082,363 A * | 7/2000 | Washburn | 128/859 |
| 6,178,967 B1 * | 1/2001 | Barnes, Sr. | 128/859 |
| 6,223,376 B1 | 5/2001 | Lee | |
| 6,247,930 B1 * | 6/2001 | Chiang et al. | 433/80 |
| 6,353,956 B1 * | 3/2002 | Berge | 15/22.1 |
| 6,428,315 B1 * | 8/2002 | Prestipino et al. | 433/45 |
| 6,505,628 B2 * | 1/2003 | Kittelsen et al. | 128/859 |

(Continued)

FOREIGN PATENT DOCUMENTS

| | | |
|---|---|---|
| EP | 1398061 A2 | 3/2004 |
| WO | 2007128848 A1 | 11/2007 |
| WO | 2009150559 A1 | 12/2009 |

*Primary Examiner* — Monica Carter
*Assistant Examiner* — Michael Jennings

(57) ABSTRACT

The mouthpiece (10) includes receiving portions for receiving teeth from the upper and lower jaws. The teeth receiving portions includes two side portions (26, 28) which are joined by flexible members (32, 34) to a front portion (30). The two side portions move laterally relative to the front portion by the flexible members to accommodate a variety of dental arch configurations.

12 Claims, 2 Drawing Sheets

U.S. PATENT DOCUMENTS

| | | | |
|---|---|---|---|
| 6,526,982 B1 * | 3/2003 | Strong | 128/848 |
| 6,584,978 B1 * | 7/2003 | Brett et al. | 128/859 |
| 6,598,605 B1 * | 7/2003 | Kittelsen et al. | 128/859 |
| 7,082,638 B2 * | 8/2006 | Koh | 15/22.1 |
| 7,125,251 B2 * | 10/2006 | Livolsi | 433/41 |
| 7,270,540 B2 * | 9/2007 | Skinner | 433/43 |
| 7,357,633 B2 * | 4/2008 | Mailyan | 433/7 |
| 7,458,810 B2 * | 12/2008 | Bergersen | 433/6 |
| 7,757,693 B2 * | 7/2010 | Toussaint | 128/848 |
| 7,810,503 B2 * | 10/2010 | Magnin | 128/848 |
| 7,963,766 B2 * | 6/2011 | Cronauer | 433/6 |
| 2003/0224313 A1 | 12/2003 | Bergersen | |
| 2004/0170941 A1 * | 9/2004 | Phan et al. | 433/6 |
| 2010/0288290 A1 * | 11/2010 | Lee et al. | 128/861 |
| 2011/0185525 A1 * | 8/2011 | Stapelbroek et al. | 15/167.1 |

* cited by examiner

SECTIONED MOUTHPIECE FOR ORAL CARE

This invention relates generally to mouthpieces useful for oral care, and more specifically concerns such a mouthpiece adapted so that it can fit a large percentage of the population.

Generally, for a mouthpiece adapted for oral care, such as teeth cleaning, it is important that the mouthpiece comfortably fit the dental arch of the user. This can include just the upper or lower jaws or both, depending upon the desired function of the mouthpiece. Actual measurements have demonstrated that the dental arch can vary significantly from person to person. Thus, it has been difficult heretofore for a single mouthpiece to fit most or even a majority of the population.

Hence, it is desirable to have a mouthpiece for oral care arranged to fit at least a majority of the population, thereby eliminating the necessity of a large number of specific mouthpiece configurations.

Accordingly, a mouthpiece for oral care applications is disclosed herein, comprising:

a mouthpiece body for receiving teeth situated in one or both of the upper and lower jaws, wherein the mouthpiece body includes at least two spaced teeth receiving portions joined by an intermediate flexible member, such that the two spaced portions can move laterally relative to each other to accommodate various dental arches.

Figure 1:
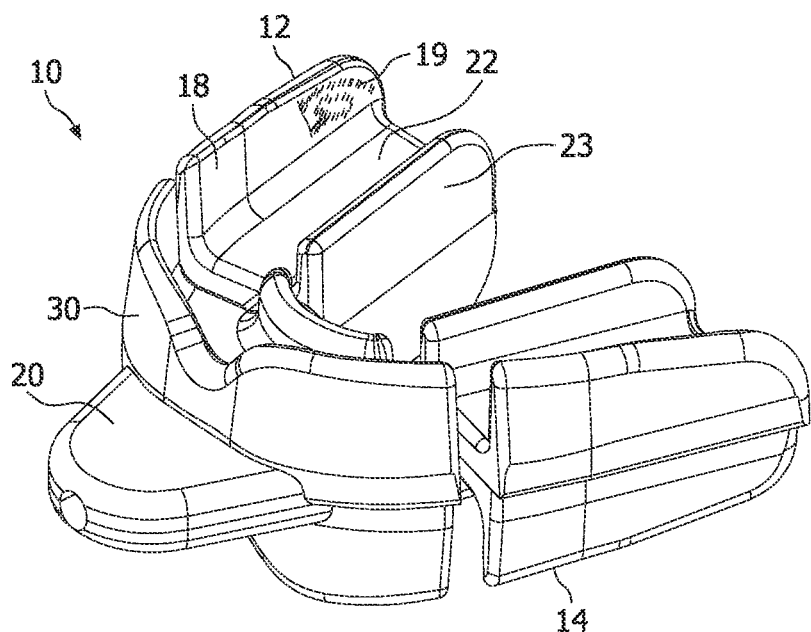
FIG. 1 is a perspective view of a mouthpiece incorporating the structure of the present invention.
Figure 2:
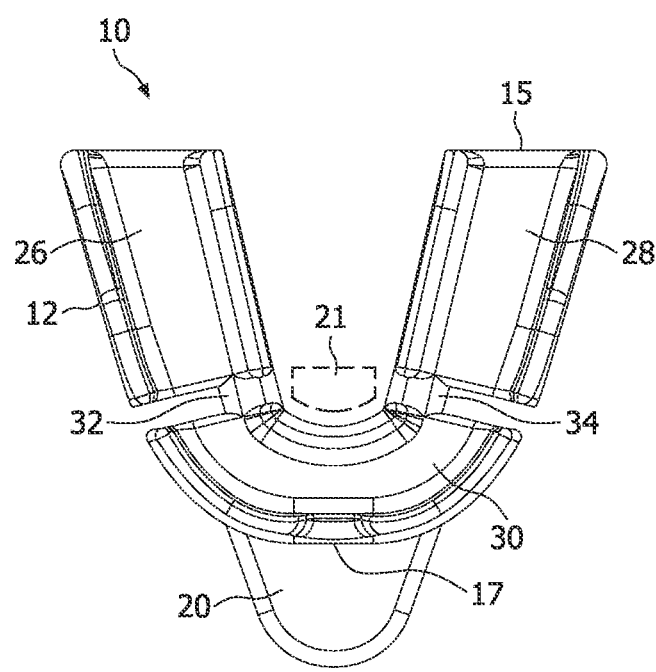
FIG. 2 is a top view of the mouthpiece of FIG. 1.

As stated above, there is a variance in dental arch configuration within the population, which typically has prevented any known mouthpiece from accommodating a substantial percentage of the population. Multiple mouthpieces having various dental arch configurations must hence be available in order to accommodate the population or a substantial portion thereof. FIGS. 1 and 2 show one embodiment of a mouthpiece which is configured and arranged to accommodate, i.e. operatively receive, a large number of different dental arches so that a single mouthpiece can be used by a large percentage of, if not virtually all, the population.

A mouthpiece body 10 has an upper portion 12 to receive teeth in the upper jaw and a lower portion 14 to receive the teeth in the lower jaw. The mouthpiece body from a posterior end 15 to an anterior end 17 is large enough to accommodate all of the teeth in the upper and lower jaws. At the anterior end 17 is a handle element 20 by which the user can conveniently insert and remove the mouthpiece body 10 into and from the mouth.

The mouthpiece body 10 can be used for a variety of oral care functions. When it is used to clean teeth, it will include bristles 19 or similar elements (shown partially in FIGS. 1 and 4) on the interior surfaces of the upper and/or lower portions, as well as a motor assembly (shown at 21) to move the bristles to produce teeth cleansing. Such a brushing structure is shown and described in detail in prior pending application Ser. No. 61/060,349, which is owned by the assignee of the present invention, the contents of which are hereby incorporated by reference. As indicated above, the upper and lower portions 12 and 14 of the mouthpiece are configured to receive teeth in such an embodiment. Typically, the upper and lower portions have a U-shaped configuration, with vertical walls 18 and 23 adapted to extend along the side surfaces of the teeth, while intermediate wall 22 fits against the horizontal surfaces of the teeth.

Figure 3:
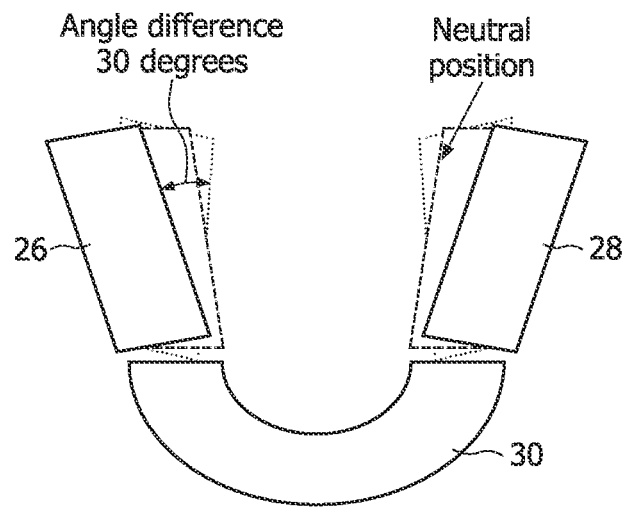
FIG. 3 is a another top view of the mouthpiece of FIGS. 1 and 2 showing a range of movement of portions of the mouthpiece.

In the embodiment of FIGS. 1 and 2, the mouthpiece body 10 includes three separate sections, two side sections 26 and 28 and an intermediate front section 30. The side sections 26 and 28 are joined, respectively, to the front section by flexible hinges 32 and 34. In the embodiment shown, the hinges are made from a silicon material, as is the remainder of the mouthpiece body. The hinges 32 and 34 are located at or near the interior vertical wall 18 of the mouthpiece and in cross-section are each approximately 7 mm square, and are approximately 3.5 mm long. In the embodiment shown, the distance between the two hinges 32 and 34 is approximately 25 mm, although this can vary. The arrangement of FIGS. 1 and 2 permits side sections 26 and 28 to move somewhat laterally relative to the front section 30 thus accommodating a variety of dental arch configurations. In the embodiment shown, the side sections move through a range of approximately 30°, as shown in FIG. 3, although this also can vary. The centerlines of the flexible hinges are typically at an angle of approximately 37° on opposite sides of the center line of the mouthpiece body when the side sections are in a neutral (relaxed) position, i.e. when the mouthpiece is out of the mouth. This angular position can vary to some extent, within the range 25°-50°. The angular position of the flexible hinges, as well as its dimensions, are important in order that the mouthpiece accommodate the greatest number of dental arches within the population.

While the embodiment shown comprises silicon, hinges that are integral with the remainder of the mouthpiece body, i.e. the side and front sections, the hinges could be of a different material than the remainder of the mouthpiece body or could be like a conventional hinge with separate elements extending from the side/front sections, rotatable about a center pin. Functionally and structurally, it is important that the two side sections of the mouthpiece be readily moveable laterally relative to the front section, in order to accommodate different dental arch configurations.

Figure 4:
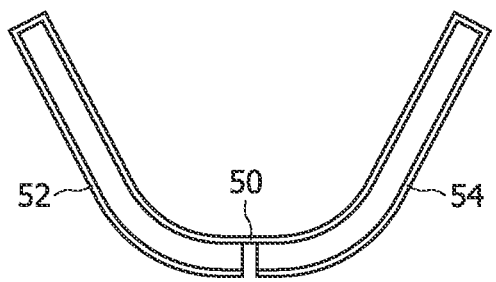
FIG. 4 is a simple top view of another embodiment of the mouthpiece.
Figure 5:
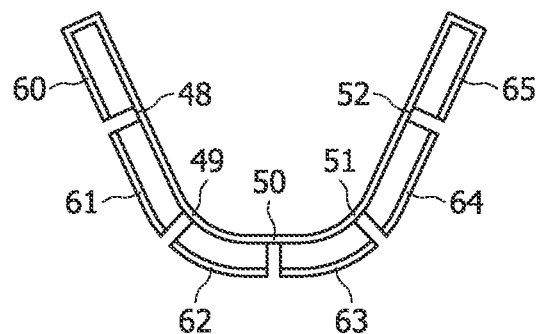
FIG. 5 is a simple top view of a further embodiment of the mouthpiece.

FIG. 4 shows a simple top view of another embodiment of the mouthpiece, in which a single central hinge 50 is used to connect to opposing (left and right) portions 52, 54 of the toothbrush body. A central hinge can also be added to the two-hinge embodiment described above in FIGS. 1 and 2 to produce a three-hinge arrangement. A still further embodiment is shown in FIG. 5, in which a mouthpiece body comprises a total of six portions 60 to 65, the portions being connected to each other by intermediate flexible hinges, 48-52. In detail, the center hinge 50 connects a first set of two side sections 62 and 63, with hinges 49 and 51 connecting sections 62 and 61 and sections 63 and 64, respectively. Hinges 48 and 52 connect sections 61 and 60 and section 64 and 65, respectively.

Figure 6:
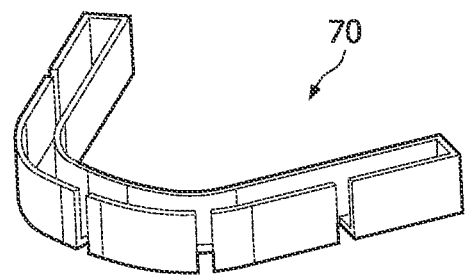
FIG. 6 is a perspective view of a mouthpiece adapted to fit just the upper jaw.

In a variation of the embodiment of FIGS. 1-3, the mouthpiece could be arranged to receive just the teeth from the upper jaw or just the teeth from the lower jaw. FIG. 6 shows such a mouthpiece 70 for just the teeth from the upper jaw, with a total of five sections connected by flexible hinges. As a further variation, instead of a single hinge providing flexible movement between adjacent sections which accommodate both upper and lower jaws, each section could comprise two parts, e.g. two part side sections relative to a single part front section, with each side section part accommodating one of the jaws. Each such part is separately hinged to the adjacent section. This arrangement provides further accommodation capability for different dental arches.

Accordingly, a mouthpiece for use in oral care applications has been disclosed which is able to accommodate a large percentage of different dental arches.

A variety of oral care applications can be accommodated with the present structure, including oral hygiene, specifically, teeth cleaning and plaque removal, but also other applications, including gum/tongue massage and various other oral care treatments, including teeth whitening, medication application and orthodontic treatment, as well as mouth guards and other safety mouthpieces. In a teeth cleaning application using bristles, it should be understood that the bristles could bridge the hinges, either with larger bristles in the hinge area, or positioned on the hinges and/or the adjacent sections of the mouthpiece body, to maintain the functionality of cleaning around the hinge areas.

Although a preferred embodiment of the invention has been disclosed herein for purposes of illustration, it should be understood that various changes, modifications and substitutions may be incorporated in the embodiment without departing from the spirit of the invention which defined by the claims which follow.

The invention claimed is:

1. A mouthpiece for oral care application, comprising:
   a mouthpiece body (10) for receiving teeth situated in both the upper and lower jaws, wherein the mouthpiece body includes at least two separate, spaced teeth receiving portions for, respectively, teeth in the upper jaw and teeth in the lower jaw, wherein the teeth receiving portions each have two ends, wherein adjacent teeth receiving portions are joined together at adjacent ends thereof by an intermediate flexible hinge member, configured and located such that the distance between adjacent teeth receiving portions at the interior vertical walls thereof is fixed, wherein the intermediate flexible hinge member is configured and arranged such that the two spaced teeth receiving portions are constrained to move primarily laterally relative to each other to accommodate various dental arches; and
   a motor assembly and elements on the teeth receiving portions included with the mouthpiece body for cleaning teeth.

2. The mouthpiece of claim 1, wherein the mouthpiece body comprises a total of three separate spaced teeth receiving portions, including a center portion (30) and two side portions (26, 28), and two intermediate flexible members which connect, respectively, the side portions to the center portion, and wherein the two side portions have centerlines which are located within a range of 25° to 50° on opposite sides of a centerline of the mouthpiece body when the side portions are at rest outside of the mouth.

3. The mouthpiece of claim 2, wherein the mouthpiece body is adapted to receive teeth from both the upper and lower jaws of a user.

4. The mouthpiece of claim 2, wherein the mouthpiece body and the intermediate flexible hinge members comprise a silicon material.

5. The mouthpiece of claim 2, wherein the intermediate flexible hinge members are positioned at an interior vertical surface (10) of the teeth receiving portions.

6. The mouthpiece of claim 2, wherein the intermediate flexible hinge members are arranged such that the teeth receiving portions are movable through an angle of approximately 30°.

7. The mouthpiece of claim 2, wherein the mouthpiece includes brush elements (19) and a system (21) for moving the brush elements to provide a cleaning function for the teeth.

8. The mouthpiece of claim 7, wherein the brush elements bridge the intermediate flexible hinge members to provide complete cleaning of the teeth.

9. The mouthpiece of claim 1, wherein the two laterally spaced teeth receiving portions (52, 54) are approximately the same size and wherein the intermediate flexible hinge member is located approximately at a centerline of the mouthpiece body.

10. The mouthpiece of claim 1, wherein the mouthpiece body includes a total of six teeth receiving portions (60-65), each of the receiving portions joined by a an intermediate flexible hinge member (48-52) to an adjacent teeth receiving portion.

11. The mouthpiece of claim 1, wherein the mouthpiece body is adapted to receive only teeth from the upper jaw of a user.

12. The mouthpiece of claim 1, wherein the mouthpiece body is adapted to receive only teeth from the lower jaw of a user.

* * * * *